(12) United States Patent
Kang et al.

(10) Patent No.: US 8,575,115 B2
(45) Date of Patent: Nov. 5, 2013

(54) CRYSTALLINE FORM I OF 3,4'5-TRIHYDROXY-STILBENE-3-β-D GLUCOSIDE

(75) Inventors: Hui Kang, Guangdong (CN); Jinhua Zhao, Guangdong (CN); Guanghui Yao, Guangdong (CN); Weizhen Zeng, Guangdong (CN); Milai Yin, Guangdong (CN); Yong Li, Guangdong (CN); Cunfang Wang, Guangdong (CN); Lijuan Zhang, Guangdong (CN); Dan Zhu, Guangdong (CN); Hong Chen, Guangdong (CN); Chuangui Huang, Guangdong (CN); Yu Man, Guangdong (CN); Jing Li, Guangdong (CN); Hanlin Feng, Guangdong (CN); Lin Yu, Guangdong (CN)

(73) Assignee: Shenzhen Neptunus Pharmaceutical Holdings Co., Ltd., Guangdong (CN)

( * ) Notice: Subject to any disclaimer, the term of this patent is extended or adjusted under 35 U.S.C. 154(b) by 959 days.

(21) Appl. No.: 12/097,321

(22) PCT Filed: Aug. 28, 2006

(86) PCT No.: PCT/CN2006/002204
§ 371 (c)(1),
(2), (4) Date: Jun. 13, 2008

(87) PCT Pub. No.: WO2007/068171
PCT Pub. Date: Jun. 21, 2007

(65) Prior Publication Data
US 2008/0293643 A1    Nov. 27, 2008

(30) Foreign Application Priority Data
Dec. 13, 2005  (CN) .......................... 2005 1 0130502

(51) Int. Cl.
*A01N 43/04* (2006.01)
*A61K 31/70* (2006.01)

(52) U.S. Cl.
USPC ........................................................ 514/25

(58) Field of Classification Search
None
See application file for complete search history.

(56) References Cited

U.S. PATENT DOCUMENTS 7,384,920 B2 * 6/2008 Li et al. .......................... 514/23

FOREIGN PATENT DOCUMENTS

| CN | 1277954 A | 12/2000 |
|---|---|---|
| CN | 1403088 A | 3/2003 |
| CN | 1431215 A | 7/2003 |
| WO | WO 03/009838 * | 2/2003 |

OTHER PUBLICATIONS

Orsini, F. et al "Isolation, synthesis and antiplatelet aggregation activity . . ." J. Nat. Prod. (1997) vol. 60, pp. 1082-1087.*
Vippagunta, S. et al "Crystalline Solids" Adv. Drug Deliv. Rev. (2001) vol. 48, pp. 3-26.*
Fujiwara, M. et al "First-principles and direct design approaches . . ." J. Proc. Control (2005) vol. 15, pp. 493-504.*
Caira, M. et al "Crystalline polymorphism of organic compounds" Topics Curr. Chem. (1998) vol. 198, pp. 163-208.*
Hillis, W. E. et al., "The Chromatographic and Spectral Properties of Stilbene Derivatives" *Journal of Chromatography* (1968) pp. 323-336, vol. 32.
Jayatilake, G. S. et al., "Kinase Inhibitors From *Polygonum cuspidatuni*" *Journal of Natural Products* (1993) pp. 1805-1810, vol. 56(10).
International Search Report dated Dec. 28, 2006.

* cited by examiner

*Primary Examiner* — Layla Bland
(74) *Attorney, Agent, or Firm* — Scully, Scott, Murphy & Presser, P.C.

(57) ABSTRACT

The present invention relates to a novel crystalline form of a Compound 3,4',5-trihydroxy-stilbene-3-β-D-glucoside (polydatin) and a method of preparation and use thereof, and to a pharmaceutical composition containing crystalline form I of 3,4',5-trihydroxy-stilbene-3-β-D-glucoside. Crystalline form I of 3,4',5-trihydroxy-stilbene-3-β-D-glucoside of the present invention has a stable crystalline morphology, a definite melting point and a good chemical stability. Such a novel form of 3,4',5-trihydroxy-stilbene-3-β-D-glucoside possesses the properties required for the preparation of solid formulations and is easily tabletable and readily formable when formulated, which allows for substantial decrease in raw materials costs, more facile operations in production and easier control over quality in industrial drug production, and moreover, better convenience in storage.

6 Claims, 6 Drawing Sheets

CRYSTALLINE FORM I OF 3,4'5-TRIHYDROXY-STILBENE-3-β-D GLUCOSIDE

TECHNICAL FIELD

The present invention relates to a novel crystalline form of Compound 3,4',5-trihydroxy-stilbene-3-β-D-glucoside (polydatin) and a method of preparation and use thereof. The present invention also relates to a pharmaceutical composition comprising crystalline form I of 3,4',5-trihydroxy-stilbene-3-β-D-glucoside.

TECHNICAL BACKGROUND 3,4',5-trihydroxy-stilbene-3-β-D-glucoside, also known as polydatin or resveratrol glucoside, is a known compound. China Patent Application No. 03117246, among other Chinese patents, describes the method of preparation of the Compound. However, the physicochemical parameters of 3,4',5-trihydroxy-stilbene-3-β-D-glucoside as reported by different references vary widely. Examples are as follows:

| References | Melting Point (° C.) | Crystallization Solvent |
|---|---|---|
| 1. China Patent Application No. 03117246 | 146~147 | Crystallization by 55%~65% ethanol followed by washing with iced water |
| 2. Fulvia Orsini, Isolation, Synthesis, and Antiplatelet Aggregation Activity of Resveratrol 3-O-β-D-Glucopyranoside and Related Compounds, J. Nat. Prod. 1997, 60, 1082~1087, (in the reference of this paper, Hillis W E, Ishikura K, J Chromatogr, 32, 323 (1968), the melting point is indicated to be 228~230° C.) | 220~225 | CHCl$_3$-MeOH 9:1 |
| 3, Gamini S. Jayatilake. Kinase Inhibitors From Polygonum Cuspidtum. Journal of Nature Products. 1993, 56(10), 1805-110. (in the reference of this paper, M. Antoni, D. M. X. Donnelly, Phytochemistry, 15, 200 (1976), the melting point is indicated to be 130~140° C.) | 135~137 | 20%~50% MeOH—H$_2$O |
| 4. Chunru Ji and Yuming Wang, Experimental techniques and Experiments of Chemistry of Chinese Medicine, Henan Publishing House of Science & Technology, 1986, p. 285. | 130~140, 225~226 (double melting points) | 30% MeOH—H$_2$O Dissolved by heating followed by being concentrated to crystallize |
| 5. Yuming Kan et. al., Experimental Operation Techniques of Chemistry of Chinese Medicine, Medical Science and Technology Publishing House of China, 1986, p. 153. | 223~226 (decomposed) | 30% MeOH—H$_2$O/ 30% EtOH—H$_2$O |

The melting points of 3,4',5-trihydroxy-stilbene-3-β-D-glucoside as reported by the above references vary widely, and the melting ranges are in most cases as wide as 5~10° C. At present, no systemic research and/or interpretation is available regarding the differences in the physicochemical properties of 3,4',5-trihydroxy-stilbene-3-β-D-glucoside as reported by different references. The inventors have discovered for the first time that 3,47,5-trihydroxy-stilbene-3-β-D-glucoside shows complex polymorphism, and the crystals of 3,4',5-trihydroxy-stilbene-3-β-D-glucoside conventionally prepared according to the references are mostly a mixture of complex polymorphic crystals and/or amorphous powders, which accounts for the generally wide melting range that is measured, and even the appearance of double melting points.

It is known that the crystalline form of a drug will have influences on the dissolution rate, solubility, hygroscopicity, stability, biosorption and even bioactivity of the drug. Therefore, the crystalline form of a drug will significantly influence the drug activity, especially that of solid oral formulations, including, inter alia, drug therapeutic activity and adverse effects. In addition, the crystalline form of a drug will affect the bulkiness of the drug, which will further influence such formulating techniques as mixing, filling, milling, pelletizing, drying, tableting and the like, and even will possibly influence aspects in close relation to application of the drug, such as the storage life of the drug.

Generally speaking, for use in drug, especially in solid drug formulations, active substances should have defined physical forms and definite physicochemical properties. Inconsistency in the physical forms and/or physicochemical properties of the active substances may lead to difficulties in the formulating techniques of solid formulations or even liquid formulations, and difficulties in the clinical use of the formulations final products due to inhomogeneous properties. It is therefore obvious that stable supply of 3,4',5-trihydroxy-stilbene-3-β-D-glucoside with definite physicochemical properties is both theoretically and practically important for the preparation of formulations, especially solid formulations, of the Compound.

DESCRIPTION OF THE INVENTION

An object of the present invention is to provide crystalline form I of 3,4',5-trihydroxy-stilbene-3-β-D-glucoside which has the properties required for the preparation of solid drug formulations.

Another object of the present invention is to provide a method of preparing crystalline form I of 3,4',5-trihydroxy-stilbene-3-β-D-glucoside.

A further object of the present invention is to provide a pharmaceutical composition containing crystalline form I of 3,4',5-trihydroxy-stilbene-3-β-D-glucoside.

A still further object of the present invention is to provide a use of crystalline form I of 3,4',5-trihydroxy-stilbene-3-β-D-glucoside in the preparation of drugs for the treatment or prevention of diseases related to microcirculatory dysfunction.

According to one aspect of the present invention, crystalline form I of 3,4',5-trihydroxy-stilbene-3-β-D-glucoside, when detected by X-ray powder diffraction (XRD) using a Cu radiation source, exhibits a XRD spectrum which at least comprises characteristic diffraction peaks with a distance of crystal face (d-value) of about 5.27±0.2, 5.05±0.2, 4.49±0.2, 4.16±0.2 and 3.84±0.2 Å respectively, each peak with a relative intensity ($I/I_o$) approximately equal to or higher than 40%. Further, crystalline form I of 3,4',5-trihydroxy-stilbene-3-β-D-glucoside of the present invention exhibits the characteristic diffraction peaks with a distance of crystal face (d-value) of about 16.7±0.2, 8.35±0.2, 7.03±0.2, 6.35±0.2, 5.27±0.2, 5.05±0.2, 4.80±0.2, 4.49±0.2, 4.16±0.2, 4.05±0.2, 3.84±0.2, 3.34±0.2, 3.27±0.2, 3.17±0.2, 3.00±0.2 and 2.78±0.2 Å respectively, each peak with a relative intensity ($I/I_o$) approximately equal to or higher than 15%.

The XRD spectrum that characterizes the crystalline forms was obtained using a RIGAKU X-ray powder diffractor (D/Max-IIIA, Cu target).

Crystalline form I of 3,4',5-trihydroxy-stilbene-3-β-D-glucoside of the present invention, when characterized using the differential scanning calorimetry (DSC) technique, exhibits a DSC maximum endotherm falling within the range of about 225° C. to about 228° C. The endothermic process is represented by a sharp endothermic peak in the USC spectrum which, for a fully dried sample, is the only significant endothermic peak observed in the DSC spectrum. There are no evident exothermic peaks in the spectrum.

The DSC spectrum was obtained using a Netzsch differential scanning calorimeter (DSC204).

In the present invention, the XRD spectrum confirms crystalline form I of 3,4',5-trihydroxy-stilbene-3-β-D-glucoside to be a crystalline product, which, in combination with the DSC spectrum suffices to verify that crystalline form I of 3,4',5-trihydroxy-stilbene-3-β-D-glucoside has a single crystalline form.

According to another aspect of the present invention, a method for preparing crystalline form I of 3,4',5-trihydroxy-stilbene-3-β-D-glucoside is provided to obtain crystalline form I of 3,4',5-trihydroxy-stilbene-3-β-D-glucoside of the present invention by recrystallizing 3,4',5-trihydroxy-stilbene-3-β-D-glucoside from a pure solvent of absolute methanol or absolute ethanol or absolute acetone, or a mixed solvent thereof acting as a crystallization solvent. The pure solvent according to the present invention is a pure anhydrous solvent. Researches have indicated that hydrous solvents may affect to different degrees the purity of a crystallization product of 3,4',5-trihydroxy-stilbene-3-β-D-glucoside and may lead to the formation of a mixture of polymorphic crystals and/or amorphous powders.

The stable crystalline morphology and definite physicochemical properties of crystalline form I of 3,4',5-trihydroxy-stilbene-3-β-D-glucoside make it available to formulate the Compound (3,4',5-trihydroxy-stilbene-3-β-D-glucoside) into tablets or other solid or even liquid formulations, which guarantees the desired application value of the Compound.

Like 3,4',5-trihydroxy-stilbene-3-β-D-glucoside, crystalline form I of 3,4',5-trihydroxy-stilbene-3-β-D-glucoside is physiologically active in improving microcirculation, lowering blood lipid and protecting against tumors.

According to a further aspect of the present invention, a pharmaceutical composition is provided, which composition comprises crystalline form I of 3,4',5-trihydroxy-stilbene-3-β-D-glucoside, and optionally, pharmaceutically acceptable carriers and/or excipients.

3,4',5-trihydroxy-stilbene-3-β-D-glucoside and its pharmaceutical composition can be used for treating diseases related to microcirculatory dysfunction, lowering blood lipid and protecting against tumors, etc. Said diseases related to microcirculatory dysfunction include shock, cardio-cerebral-vascular disease, sense organs diseases, diabetes complications, thromboangiitis obliterans, external hemorrhoid associated with blood circulation disturbance, skin trauma or burns, etc., for instance, burns, trauma, septic shock as well as myocardial ischemia, brain hypoxia, diabetes complications, glaucoma, hearing impairment due to microcirculatory dysfunction, hemorrhoid, femoral head ischemic necrosis, thromboangiitis obliterans, hepatic cirrhosis, chronic ulcer, skin burns etc. The pharmaceutical effect of 3,4',5-trihydroxy-stilbene-3-β-D-glucoside has been elaborately described in China Patent Application No. 02134928.2 by the applicant and the references of the prior art recited therein, which have been incorporated herein as references.

The above-said pharmaceutical composition can be further formulated into administrable forms using conventional formulation methods, including orally or parenterally administrable forms. The administrable forms shall contain a therapeutically effective amount of crystalline form I of 3,4',5-trihydroxy-stilbene-3-β-D-glucoside. By "therapeutically effective amount", it means an amount of crystalline form I of 3,4',5-trihydroxy-stilbene-3-β-D-glucoside of the present invention which is effective for improving or alleviating symptoms of the diseases, or for repressing or blocking the development of the diseases. The pharmaceutical composition of the present invention can contain a unit dosage of crystalline form I of 3,4',5-trihydroxy-stilbene-3-β-D-glucoside, which is typically 1-1,000 mg, preferably 50-250 mg.

The administrable compositions can be in the form of a tablet, a capsule, a granule, a lozenge, a suppository, a patch, a gel or a powder. The preferred formulations are tablets and capsules. These administrable compositions may also be prepared into sustained/controlled release formulations or targeted formulations depending on needs.

Dosage forms for oral administration can be tablets and capsules. They may contain convention excipients, e.g. binders such as syrup, dextrin, starch slurry, acacia, gelatin, sorbitol, tragacanth, hydroxypropyl methylcellulose or polyvinylpyrrolidone; fillers such as lactose, sucrose, corn starch, calcium phosphate, sorbitol, mannitol, microcrystalline cellulose, calcium sulfate or glycine; tableting lubricant such as magnesium stearate; disintegrant such as croscarmellose sodium, starch, polyvinylpyrrolidone, crospovidone, low-substitution sodium starch glycolate, hydroxypropyl cellulose or microcrystalline cellulose; or pharmaceutically acceptable wetting agents such as sodium dodecyl sulfate, water, ethanol and the like. The dosage forms may also be dyed using any pharmaceutically acceptable colorant to improve their appearance and/or facilitate patient identification of the product and unit dosage level.

Selection of the above-mentioned carriers and/or excipients and the amounts for use may be readily determined by those skilled in the art based upon experience and consideration of standard procedures and reference works in the art.

In summary, the present invention prepares crystalline form I of 3,4',5-trihydroxy-stilbene-3-β-D-glucoside which has a stable crystalline morphology, a definite melting point and a good chemical stability. Such a novel form of 3,4',5-trihydroxy-stilbene-3-β-D-glucoside possesses the properties required for the preparation of solid formulations and is easily tabletable and readily formable in formulation, which allows for substantial decrease in raw materials costs, more facile operations in production and easier control over quality in industrial drug production, and moreover, better convenience in storage.

The detection conditions for the samples in the Examples are as follows: XRD is conducted on a RIGAKU X-ray powder diffractor (D/Max-IIIA) with Cu—Kα radiation, 2θ=2-60° C.; DSC is conducted on a NETZSCH differential scanning calorimeter (DSC204) with a measurement range of 0-250° C. More detailed detection parameters are shown in the accompanied table I of the Examples.

BEST MODES FOR CARRYING OUT THE INVENTION

Preparation of Crystalline Form I of 3,4',5-trihydroxy-stilbene-3-β-D-glucoside

Example 1

3,4',5-trihydroxy-stilbene-3-β-D-glucoside raw compound can be prepared using the method described in China Patent Application No. 03117246; the solvent methanol can be double distilled to obtain refined methanol. 150 g of any crystalline or amorphous form of 3,4',5-trihydroxy-stilbene-3-β-D-glucoside was added into about 1 L of the refined methanol solvent and dissolved. The resulting solution was filtered. The filtrate was concentrated under reduced pressure (0.1 Mpa, 55° C.), which was then dried to constant weight (0.1 Mpa, room temperature) to obtain 126 g solid with a yield of 84.0%.

Figure 1:
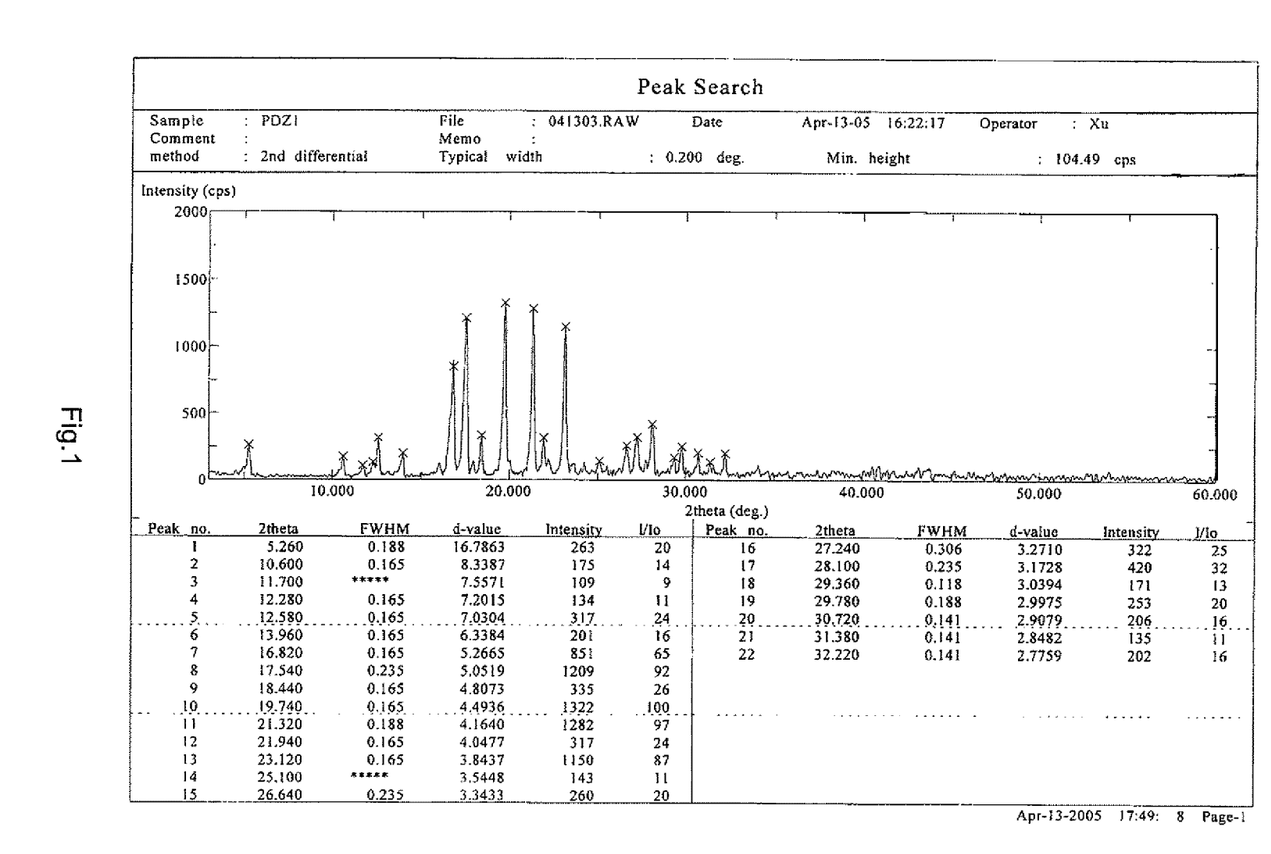
FIG. 1 shows the XRD spectrum of the sample in Example 1.
Figure 2:
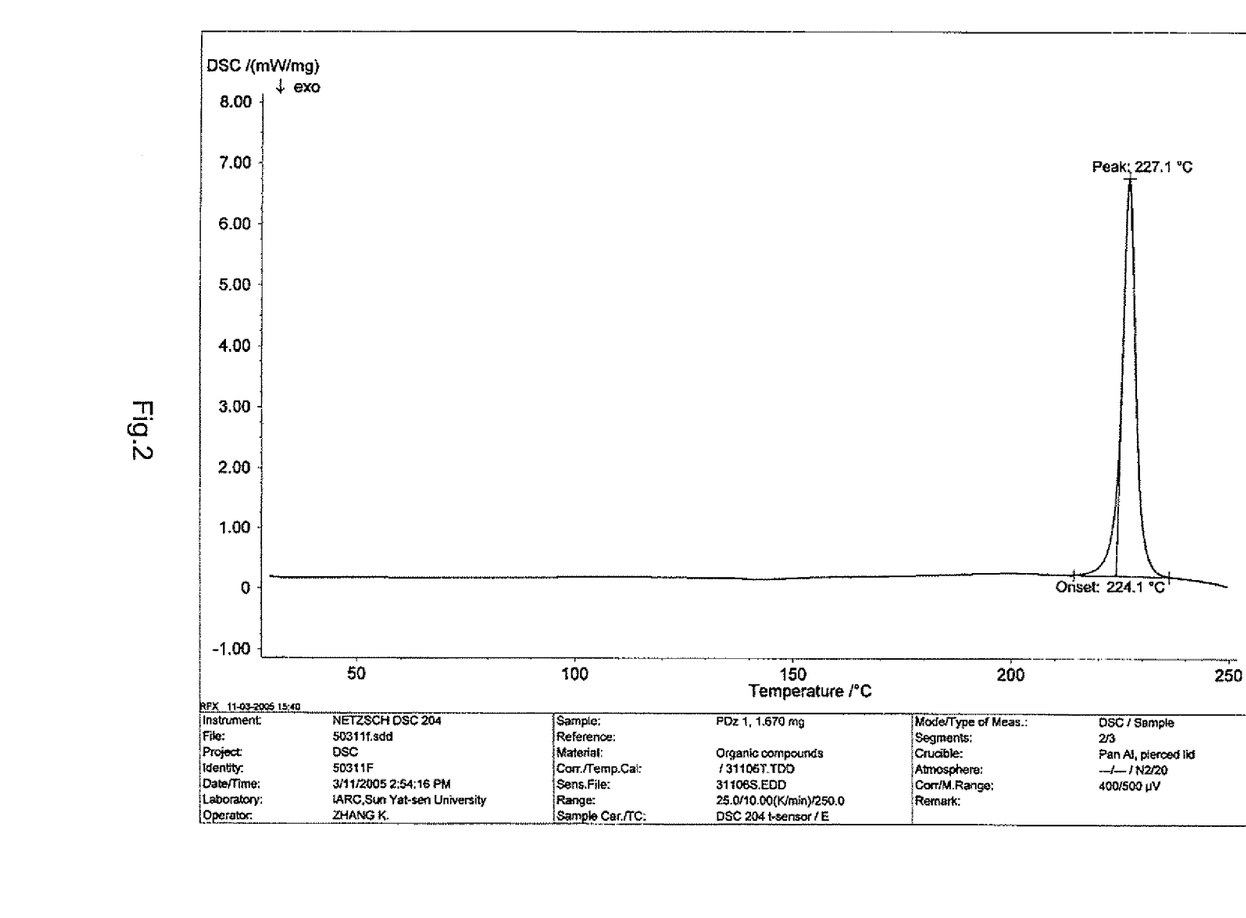
FIG. 2 shows the DSC spectrum of the sample in Example 1.

The XRD spectrum of the sample is as shown in FIG. 1 and the DSC spectrum is as shown in FIG. 2.

Example 2

3,4',5-trihydroxy-stilbene-3-β-D-glucoside raw compound can be prepared using the method described in China Patent Application No. 03117246. 200 g of any crystalline or amorphous form of 3,4',5-trihydroxy-stilbene-3-β-D-glucoside was added into about 1.5 L of absolute ethanol and dissolved. The resulting solution was filtered. The filtrate was concentrated under reduced pressure (0.1 Mpa, 55° C.), which was then dried to constant weight (0.1 Mpa, room temperature) to obtain 153 g solid with a yield of 76.5%.

Figure 3:
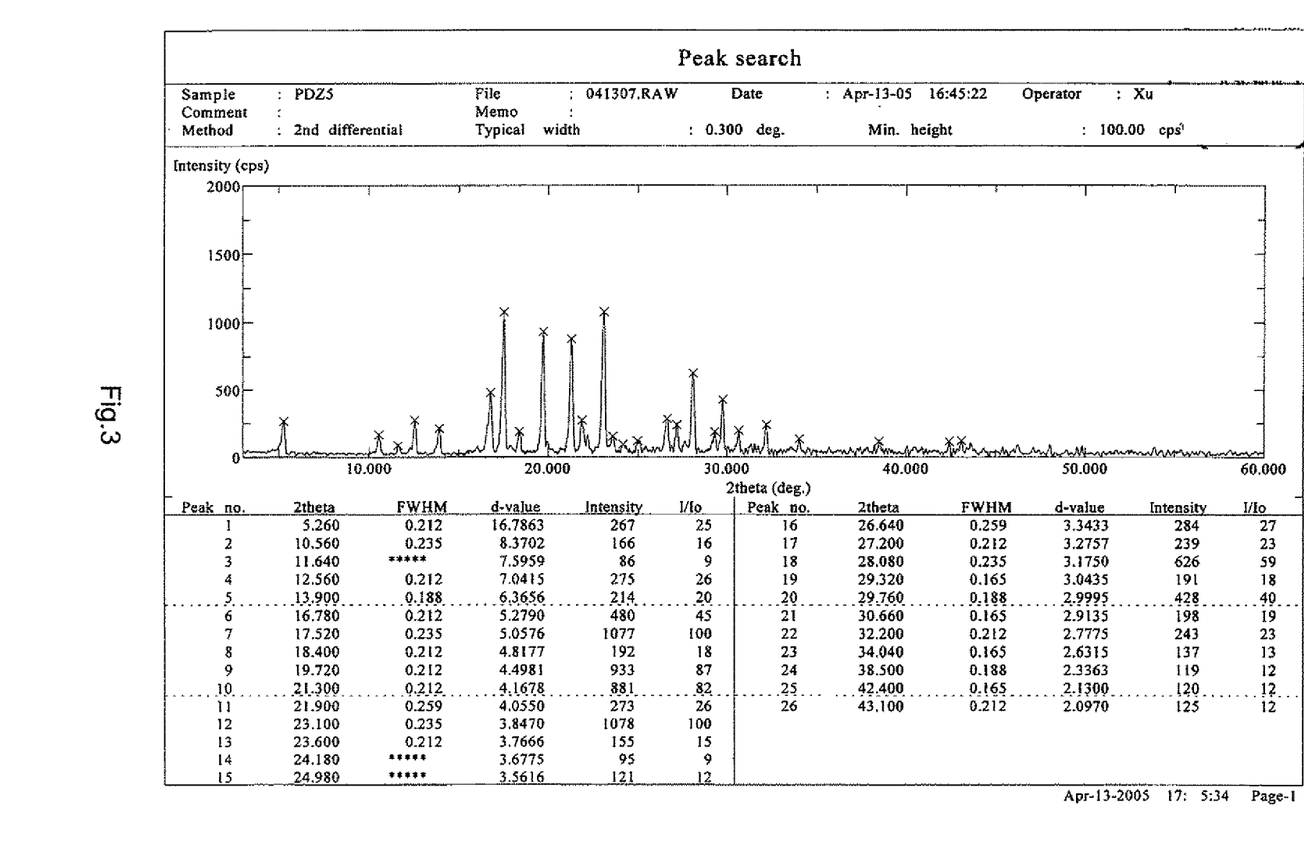
FIG. 3 shows the XRD spectrum of the sample in Example 2.
Figure 4:
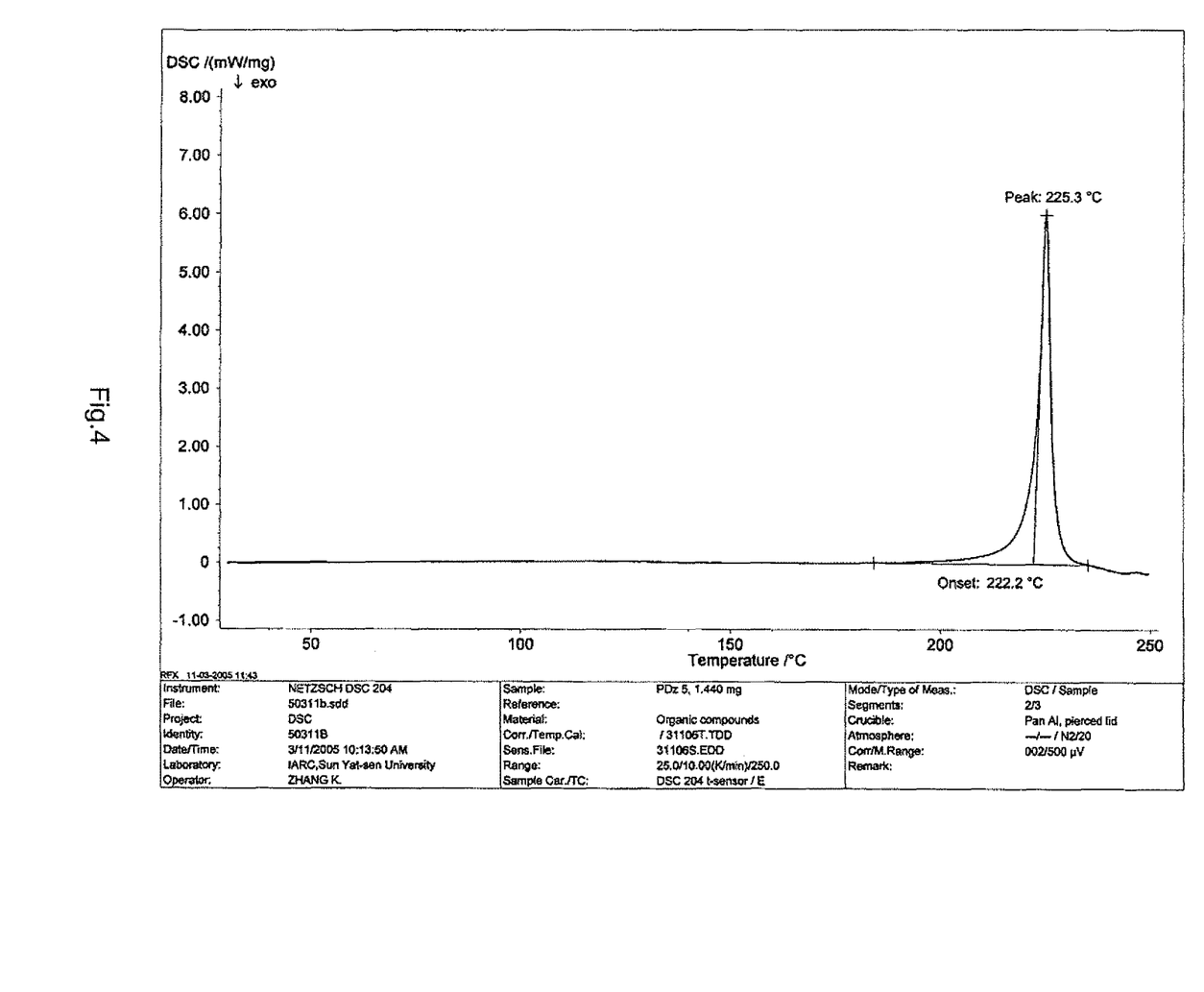
FIG. 4 shows the DSC spectrum of the sample in Example 2.

The XRD spectrum of the sample is as shown in FIG. 3 and the DSC spectrum is as shown in FIG. 4.

Example 3

0.1% potassium permanganate was added into the solvent of acetone. The mixture was sufficiently shaken and then heated to reflux for 4 hours until the color of potassium permanganate remained unfaded. The mixture was dried over anhydrous sodium sulfate and double distilled to obtain the refined acetone solvent. 50 g of any crystalline or amorphous form of 3,4',5-trihydroxy-stilbene-3-β-D-glucoside was added into about 1.5 L of the refined acetone solvent and dissolved. The resulting solution was filtered. The filtrate was concentrated under reduced pressure (0.1 Mpa, 50° C.), which was then dried to constant weight (0.1 Mpa, room temperature) to obtain 43 g solid with a yield of 86.0%.

Figure 5:
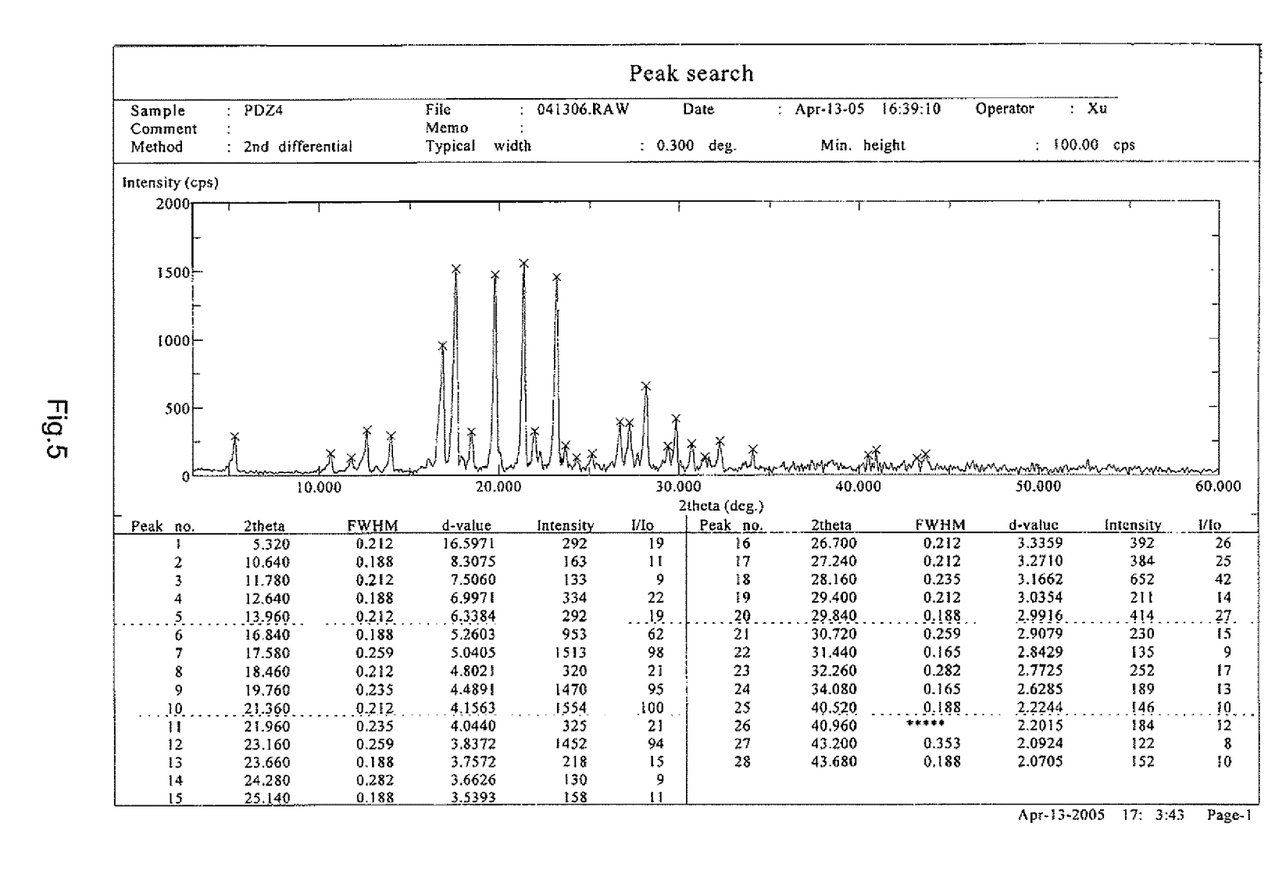
FIG. 5 shows the XRD spectrum of the sample in Example 3.
Figure 6:
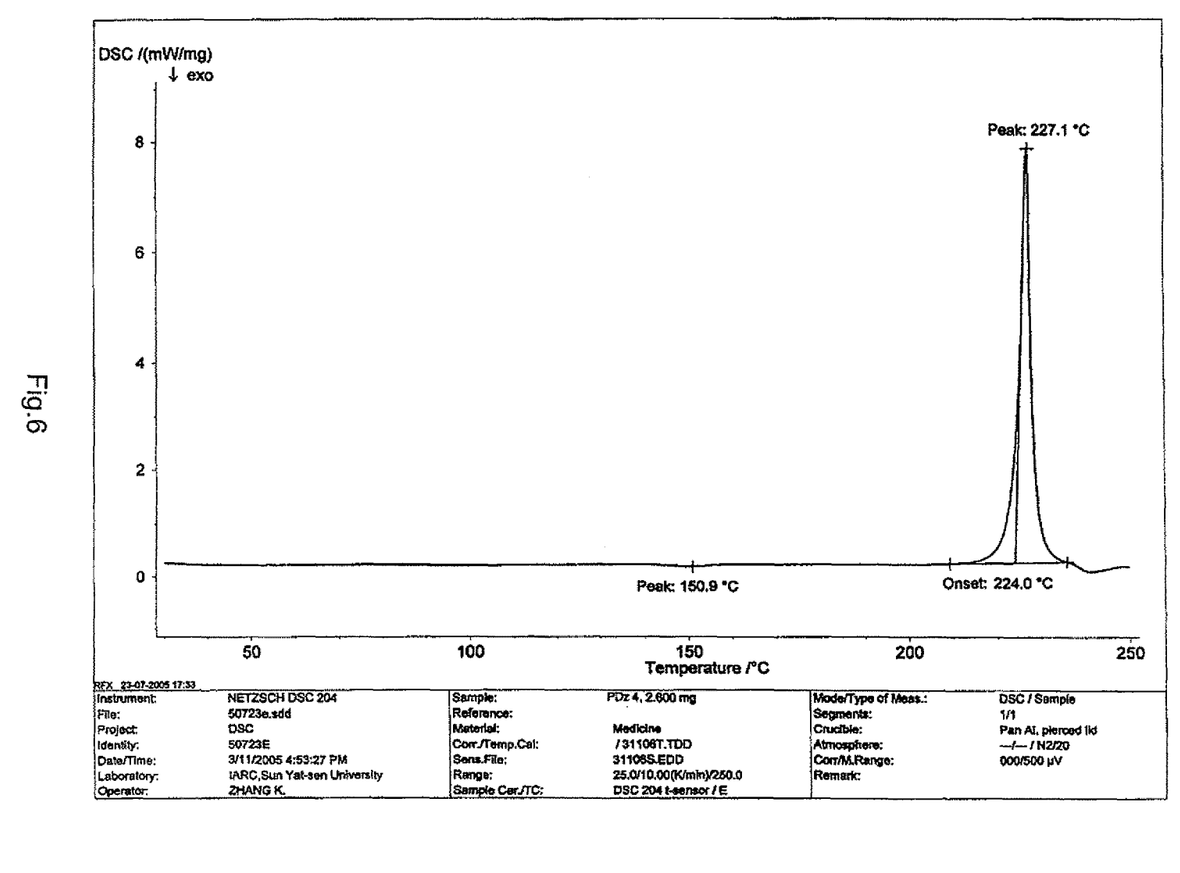
FIG. 6 shows the DSC spectrum of the sample in Example 3.

The XRD spectrum of the sample is as shown in FIG. 5 and the DSC spectrum is as shown in FIG. 6.

The major diffraction peak values in the XRD spectra of the samples of Example 1, 2 and 3 are shown in Table 1.

TABLE 1

Diffraction peak values in the XRD spectra of the samples in the Examples

| Sample of Example 1 | | | | Sample of Example 2 | | | | Sample of Example 3 | | | |
| --- | --- | --- | --- | --- | --- | --- | --- | --- | --- | --- | --- |
| Peak No. | 2θ | d-value | $I/I_0$ | Peak No. | 2θ | d-value | $I/I_0$ | Peak No. | 2θ | d-value | $I/I_0$ |
| 1 | 5.26 | 16.8 | 23 | 1 | 5.26 | 16.8 | 25 | 1 | 5.32 | 16.6 | 19 |
| 2 | 10.6 | 8.37 | 14 | 2 | 10.6 | 8.37 | 16 | 2 | 10.6 | 8.31 | 11 |
| 4 | 12.6 | 7.04 | 27 | 4 | 12.6 | 7.04 | 26 | 4 | 12.6 | 7.00 | 22 |
| 5 | 13.9 | 6.37 | 22 | 5 | 13.9 | 6.37 | 20 | 5 | 14.0 | 6.34 | 19 |
| 7 | 16.8 | 5.28 | 54 | 6 | 16.8 | 5.28 | 45 | 6 | 16.8 | 5.26 | 62 |
| 8 | 17.5 | 5.05 | 100 | 7 | 17.5 | 5.06 | 100 | 7 | 17.6 | 5.04 | 98 |
| 9 | 18.4 | 4.81 | 18 | 8 | 18.4 | 4.82 | 18 | 8 | 18.5 | 4.80 | 21 |
| 10 | 19.7 | 4.50 | 81 | 9 | 19.7 | 4.50 | 87 | 9 | 19.8 | 4.49 | 95 |
| 11 | 21.3 | 4.17 | 88 | 10 | 21.3 | 4.17 | 82 | 10 | 21.4 | 4.16 | 100 |
| 12 | 21.9 | 4.06 | 22 | 11 | 21.9 | 4.06 | 26 | 11 | 22.0 | 4.04 | 21 |
| 13 | 23.1 | 3.84 | 87 | 12 | 23.1 | 3.85 | 100 | 12 | 23.2 | 3.84 | 94 |
| 16 | 26.6 | 3.34 | 29 | 16 | 26.6 | 3.34 | 27 | 16 | 26.7 | 3.34 | 26 |
| 17 | 27.2 | 3.28 | 19 | 17 | 27.2 | 3.28 | 23 | 17 | 27.2 | 3.27 | 25 |
| 18 | 28.1 | 3.17 | 45 | 18 | 28.1 | 3.18 | 59 | 18 | 28.2 | 3.17 | 42 |

TABLE 1-continued

Diffraction peak values in the XRD spectra of the samples in the Examples

| Sample of Example 1 | | | | Sample of Example 2 | | | | Sample of Example 3 | | | |
|---|---|---|---|---|---|---|---|---|---|---|---|
| Peak No. | 2θ | d-value | I/I₀ | Peak No. | 2θ | d-value | I/I₀ | Peak No. | 2θ | d-value | I/I₀ |
| 20 | 29.7 | 3.00 | 23 | 20 | 29.8 | 3.00 | 40 | 20 | 29.8 | 2.99 | 27 |
| 22 | 32.2 | 2.78 | 14 | 22 | 32.2 | 2.78 | 23 | 23 | 32.3 | 2.77 | 17 |

Preparation of Solid Pharmaceutical Formulations

Example 4

Tablet Formula:

| Ingredients | Amounts |
|---|---|
| crystalline form I of 3,4',5-trihydroxy-stilbene-3-β-D-glucoside (Example 1) | 112 g |
| Starch | 20 g |
| Lactose | 40 g |
| Microcrystalline cellulose | 21 g |
| Magnesium stearate | 2 g |
| Formulated into | 1,000 tablets |

Formulating method: the ingredients of the above formula were blended and directly tableted into tablets by conventional formulating methods.

Example 5

Capsule Formula:

| Ingredients | Amounts |
|---|---|
| crystalline form I of 3,4',5-trihydroxy-stilbene-3-β-D-glucoside (Example 2) | 112 g |
| Lactose | 40 g |
| Dextrin | 10 g |
| Starch (120 mesh) | 25 g |
| Micro-powder silica gel | 3 g |
| 3% HPMC | Suitable amount |
| Formulated into | 1,000 capsules |

Formulating method: crystalline form I of 3,4',5-trihydroxy-stilbene-3-β-D-glucoside (Example 2) was mixed homogeneously with starch, lactose and dextrin by repeating equal volume mix method, into which the pre-formulated HPMC solution was added to produce a soft material which was granulated by passing through a 20-mesh sieve. The granules generated therefrom were dried at 60° C. for 30 minutes before being passed through an 18-mesh sieve into homogeneous granules into which micro-powder silica gel was added, which was mixed sufficiently to be capsulized into No. 2 capsules.

The above description about the best modes for carrying out the invention is not confined to the present invention. Persons skilled in the art can make various changes or modifications according to the present invention if only not departing from the spirit of the present invention, which will fall into the scope of the appended claims all the same.

The invention claimed is:

1. Isolated single crystalline form I of 3,4',5-trihydroxy-stilbene-3-β-D-glucoside, characterized in that said crystalline form exhibits a maximum DSC endotherm falling within the range of 225° C. to 228° C., and when detected by X-ray powder diffraction (XRD) using a Cu radiation source exhibits a XRD spectrum which at least comprises characteristic diffraction peaks with a distance of crystal face (d-value) of 5.27±0.2, 5.05±0.2, 4.49±0.2, 4.16±0.2 and 3.84±0.2 Å respectively.

2. The isolated single crystalline form I of 3,4',5-trihydroxy-stilbene-3-β-D-glucoside according to claim 1, characterized in that said crystalline form when detected by X-ray powder diffraction (XRD) using a Cu radiation source exhibits a XRD spectrum which comprises characteristic diffraction peaks with a distance of crystal face (d-value) of 16.7±0.2, 8.35±0.2, 7.0±0.2, 6.35±0.2, 5.27±0.2, 5.05±0.2, 4.80±0.2, 4.49±0.2, 4.16±0.2, 4.05±0.2, 3.84±0.2, 3.34±0.2, 3.27±0.2, 3.17±0.2, 3.00±0.2 and 2.78±0.2 Å respectively.

3. A method for preparing the isolated single crystalline form I of 3,4',5-trihydroxy-stilbene-3-β-D-glucoside according to claim 1, said method comprising the step of recrystallizing 3,4',5-trihydroxy-stilbene-3-β-D-glucoside from a pure solvent of absolute methanol or absolute ethanol or absolute acetone, acting as a crystallization solvent to obtain crystalline form I of 3,4',5-trihydroxy-stilbene-3-β-D-glucoside.

4. A pharmaceutical composition, characterized in that said composition contains single crystalline form I of 3,4',5-trihydroxy-stilbene-3-β-D-glucoside according to claim 1 and a pharmaceutically acceptable carrier or excipient, and that said composition is a solid formulation.

5. A method for treatment of a disease related to microcirculatory dysfunction in a subject, comprising administering to said subject the isolated single crystalline form I of 3,4',5-trihydroxy-stilbene-3-β-D-glucoside according to claim 1 or 2.

6. The method according to claim 5, characterized in that said disease related to microcirculatory dysfunction is selected from the group consisting of shock, cardio-cerebral-vascular disease, sense organs diseases, diabetes complications, thromboangiitis obliterans, external hemorrhoid associated with blood circulation disturbance, skin trauma and burns.

* * * * *